US011344345B2

(12) United States Patent
May et al.

(10) Patent No.: US 11,344,345 B2
(45) Date of Patent: May 31, 2022

(54) ORTHOPAEDIC FIXATION DEVICE, SYSTEM AND METHOD

(71) Applicant: Jace Medical, LLC, Warsaw, IN (US)

(72) Inventors: Justin James May, Leesburg, IN (US); Scott Steffensmeier, Winona Lake, IN (US); Jason F. Detweiler, Warsaw, IN (US)

(73) Assignee: Jace Medical, LLC, Warsaw, IN (US)

( * ) Notice: Subject to any disclaimer, the term of this patent is extended or adjusted under 35 U.S.C. 154(b) by 295 days.

(21) Appl. No.: 16/580,331

(22) Filed: Sep. 24, 2019

(65) Prior Publication Data

US 2020/0015869 A1 Jan. 16, 2020

Related U.S. Application Data

(62) Division of application No. 14/524,922, filed on Oct. 27, 2014, now Pat. No. 10,441,329.

(60) Provisional application No. 61/896,376, filed on Oct. 28, 2013, provisional application No. 62/039,672, filed on Aug. 20, 2014.

(51) Int. Cl.
A61B 17/80 (2006.01)
A61B 17/15 (2006.01)
A61B 17/17 (2006.01)
A61B 17/70 (2006.01)
(Continued)

(52) U.S. Cl.
CPC .......... A61B 17/8023 (2013.01); A61B 17/15 (2013.01); A61B 17/1728 (2013.01); A61B 17/7059 (2013.01); A61B 17/8004 (2013.01); A61B 17/808 (2013.01); A61B 17/8009 (2013.01); A61B 17/8033 (2013.01); A61B 17/8061 (2013.01); A61B 17/8076 (2013.01); (Continued)

(58) Field of Classification Search
CPC . A61B 17/80; A61B 17/8004; A61B 17/8009; A61B 17/8014; A61B 17/8023; A61B 17/8061; A61B 17/8076; A61B 17/808
See application file for complete search history.

(56) References Cited

U.S. PATENT DOCUMENTS 4,072,278 A 2/1978 Petersen
5,484,439 A 1/1996 Olson et al.
(Continued)

OTHER PUBLICATIONS

International Search Report for PCT/US2014/062441 dated Mar. 25, 2015.

Primary Examiner — Si Ming Ku
(74) Attorney, Agent, or Firm — Schwegman Lundberg & Woessner, P.A.

(57) ABSTRACT

An implantable fixation device for rejoining opposed portions of a separated bone. The device including two corresponding plates that are configured to be aligned and coupled to a bone, such as a sternum, pre-resection of the bone or prior to cutting/separating the bone. The placement of the corresponding plates provides a gap between the edges of the plates that face one another allowing for and guiding a cutting tool for separating the bone. After the bone has been cut and the desired surgical procedure performed, the plates also assist in realigning and fixation of the bone portions. At least one plate includes a ratchet mechanism that is configured to tighten a locking element and draw the two plates together and into alignment with one another.

9 Claims, 17 Drawing Sheets

(51) Int. Cl.
 *A61B 17/56* (2006.01)
 *A61B 17/68* (2006.01)
(52) U.S. Cl.
 CPC ..... *A61B 17/8057* (2013.01); *A61B 2017/564* (2013.01); *A61B 2017/681* (2013.01)

(56) References Cited

U.S. PATENT DOCUMENTS

| | | | |
|---|---|---|---|
| 5,827,286 A | 10/1998 | Incavo et al. | |
| 5,849,012 A | 12/1998 | Abboudi | |
| 5,894,843 A | 4/1999 | Benetti et al. | |
| 5,925,049 A | 7/1999 | Gustilo et al. | |
| 6,007,538 A | 12/1999 | Levin | |
| 6,051,007 A | 4/2000 | Hogendijk et al. | |
| 6,355,036 B1 | 3/2002 | Nakajima | |
| 6,471,706 B1 | 10/2002 | Schumacher et al. | |
| 6,666,867 B2 | 12/2003 | Ralph et al. | |
| 6,821,279 B2 | 11/2004 | Di Emidio | |
| 6,872,210 B2 | 3/2005 | Hearn | |
| 7,033,377 B2 | 4/2006 | Miller, III | |
| 7,044,952 B2 | 5/2006 | Michelson | |
| 7,156,847 B2 | 1/2007 | Abramson | |
| 7,166,109 B2 | 1/2007 | Biedermann et al. | |
| 7,214,226 B2 | 5/2007 | Alleyne | |
| 7,291,152 B2 | 11/2007 | Abdou | |
| 7,479,143 B2 | 1/2009 | Suh et al. | |
| 7,540,874 B2 | 6/2009 | Trumble et al. | |
| 7,604,638 B2 | 10/2009 | Jacene et al. | |
| 7,621,914 B2 | 11/2009 | Ralph et al. | |
| 7,635,364 B2 | 12/2009 | Barrall et al. | |
| 7,641,675 B2 | 1/2010 | Lindemann et al. | |
| 7,670,361 B2 | 3/2010 | Nesper et al. | |
| 7,695,473 B2 | 4/2010 | Ralph et al. | |
| 7,749,256 B2 | 7/2010 | Farris et al. | |
| 7,780,672 B2 | 8/2010 | Metzger et al. | |
| 7,993,375 B2 | 8/2011 | Bae et al. | |
| 8,029,543 B2 | 10/2011 | Young et al. | |
| 8,128,628 B2 | 3/2012 | Freid et al. | |
| 8,133,227 B2 | 3/2012 | Morales et al. | |
| 8,206,390 B2 | 6/2012 | Lindemann | |
| 8,257,355 B2 | 9/2012 | Chin et al. | |
| 8,282,644 B2 | 10/2012 | Edwards | |
| 8,348,949 B2 | 1/2013 | Butler et al. | |
| 8,366,754 B2 | 2/2013 | Teague et al. | |
| 8,388,663 B2 | 3/2013 | Busch, Jr. et al. | |
| 8,435,265 B2 | 5/2013 | Konieczynski et al. | |
| 8,486,079 B2 | 7/2013 | Heavener et al. | |
| 8,518,089 B2 | 8/2013 | Gabele | |
| 8,523,861 B2 | 9/2013 | Kiritsis | |
| 8,585,742 B2 | 11/2013 | Windolf | |
| 8,636,738 B2 | 1/2014 | McClintock et al. | |
| 8,652,142 B2 | 2/2014 | Geissler | |
| 2004/0097938 A1 | 5/2004 | Alleyne | |
| 2006/0122606 A1 | 6/2006 | Wolgen | |
| 2006/0235398 A1 | 10/2006 | Farris et al. | |
| 2009/0131987 A1 | 5/2009 | Matityahu | |
| 2010/0057127 A1 | 3/2010 | McGuire et al. | |
| 2010/0121328 A1 | 5/2010 | Reitzig et al. | |
| 2010/0198221 A1 | 8/2010 | Hearn | |
| 2011/0034958 A1 | 2/2011 | Anderson et al. | |
| 2011/0082459 A1* | 4/2011 | Aravot | A61B 17/1789 606/79 |
| 2011/0238068 A1 | 9/2011 | Bemsteiner | |
| 2012/0109135 A1 | 5/2012 | Bailey | |
| 2012/0265203 A1 | 10/2012 | Angelucci et al. | |
| 2012/0316562 A1 | 12/2012 | Costa | |
| 2013/0090695 A1 | 4/2013 | Bernstein et al. | |
| 2013/0204310 A1 | 8/2013 | Roman et al. | |
| 2013/0253592 A1 | 9/2013 | Larche et al. | |
| 2013/0282064 A1 | 10/2013 | Amin | |
| 2013/0304067 A1 | 11/2013 | Hess et al. | |
| 2014/0039561 A1 | 2/2014 | Weiner et al. | |

* cited by examiner

ORTHOPAEDIC FIXATION DEVICE, SYSTEM AND METHOD

CROSS REFERENCE TO RELATED APPLICATIONS

This is a division of U.S. patent application Ser. No. 14/524,922, entitled "ORTHOPAEDIC FIXATION DEVICE, SYSTEM AND METHOD", filed Oct. 27, 2014, which is incorporated herein by reference, and which claimed benefit of U.S. Provisional Patent Application Ser. No. 61/896,376, filed Oct. 28, 2013, and U.S. Ser. No. 62/039,672, filed Aug. 20, 2014, which are incorporated herein by reference.

BACKGROUND OF THE INVENTION

1. Field of the Invention

The invention relates generally to orthopaedic fixation devices, systems and methods of such fixation, and particularly regarding use in bone fixation where adjacent sections of a bone, such as a resected bone, are intended to be rejoined.

2. Description of the Related Art

In some surgical procedures involving bones, for instance, the procedure may involve separating a bone into portions, which are thereafter reunited. This happens, for instance, in entries into the chest cavity, as for heart surgery, where the sternum is required to be separated along its length (re-sected), in the transverse plane, or a combination of the two. There may be other instances where a bone has undergone fracturing through some trauma, and is thereafter to have portions rejoined for proper healing. While discussed herein largely in the context of bones, it will nonetheless be understood that aspects of the invention hereafter described may be applicable to other body parts. Furthermore, the surgical procedure could involve angled or other cuts, and not just a situation where the bone is divided along a length.

The bones or skeletal tissue, or combinations of bone and tissue, can be held secure to one another in adjacency using a fixation device, or system. The system is desirably designed that in the event that subsequent surgery is required, as in an emergency reentry to the chest cavity, the fixation device may be opened quickly and easily with as little harm to the patient as possible. Many kinds of conventional fixation devices of the foregoing type include wires or cables that are organized to pull the bone portions together, laterally across a divide or fracture. These types of fixation devices can be relatively complex to emplace, and require more effort than desired to undue in the event of an emergency. They are also typically emplaced post-resection.

SUMMARY OF THE INVENTION

A device for guiding separation of and rejoining opposed portions of a bone where the portions have been separated, as in a surgical procedure, is disclosed. In an embodiment, the device includes a first plate configured to be disposed on and coupled to the bone and a second plate configured to be disposed on and coupled to the bone and spaced a distance from the first plate. The space allows a cutting tool to be used to create a divide in the bone between the first and second plates. That is, in this form of the invention, the fixation device is emplaced before the bone is separated.

The first plate includes a first face, a ratchet mechanism on a top portion of the first plate facing away from the bone, and a first fastener aperture configured to receive a first fastener to couple the first plate to the bone. The second plate includes a second face configured to oppose and face the first face when the first and second plates are coupled to the bone, and a second fastener aperture configured to receive a second fastener to couple the second plate to the bone.

The device further includes a locking element that is engageable with the ratchet mechanism and the second plate. The locking element is configured to be coiled in response to operation of the ratchet mechanism to draw the first and second plates together to close the divide.

The ratchet mechanism in one form may include a ratchet recess in the top portion of the first plate and a ratchet wheel disposed in and removable from the ratchet recess. The ratchet recess includes a plurality of teeth around a circumference of the ratchet recess that extend radially inward towards a center of the ratchet recess. The ratchet wheel includes a pawl or pawl-like element configured to engage the ratchet teeth and allow the ratchet wheel to rotate in a first direction while preventing rotation in an opposite direction.

The first plate may further include a boss extending in an upward direction from a central portion of the ratchet recess, and a protrusion proximal to a top edge of the boss extending radially outward from a center of the boss, wherein the first fastener aperture extends through the boss. The ratchet wheel includes a central aperture having a ledge extending substantially circumferentially around the central aperture and extending radially inward toward a center of the central aperture. The central aperture is configured to receive the boss. A cut-out formed in the ledge is configured to allow the protrusion to pass through the central aperture when the cut-out and the protrusion are aligned, and the protrusion extends over the ledge when the ratchet wheel is disposed in the ratchet recess and the cut-out and the protrusion are misaligned.

The device may further include a pin configured to be inserted into a pin aperture extending through the second plate in a substantially perpendicular direction to the longitudinal axis of the second plate. The pin includes a deflectable prong and the second plate includes first and second prong receptacles. The first prong receptacle communicates with the pin aperture and is located distal to the second face. The second prong receptacle communicates with the pin aperture and is located proximal to the second face. The pin is in a first position in which an end of the pin is held within the pin aperture when the deflectable prong is engaged with the first prong receptacle; and a second position in which the end of the pin extends beyond the second face when the deflectable prong is engaged with the second prong receptacle.

The first plate may include a pin receptacle in the first face that is configured to align with the pin aperture and receive the end of the pin when the first and second plate are coupled to the bone and the divide is closed. The pin receptacle has a depth configured to cause the end of the pin to contact a bottom of the pin receptacle when the divide is closed to maintain the first and second plates spaced the distance apart.

It will be understood that the invention can be embodied in other configurations. While described in the context of two interengaging plates, these parts need not be plates per se, but could be in other shapes. Plates have been used in the current environment described hereafter, which is particular, but not limited, to a sternal resection. The sternum presents a rather planar outward facing surface, hence a plate-like structure for the device is particularly useful.

Conceptually, however, the broad concept is in one aspect to have two (or perhaps more) parts for the device that can be emplaced, either before or after the surgical separation (or break) across which the device will function to rejoin the separated parts. The device in this form has a ratchet mechanism which serves to draw the parts of the device together, and thus place the bone parts back into rough engagement. The ratchet mechanism could be located on an outward facing surface of the device, or could be formed internally, with a tool access area for turning the ratchet wheel. Preferably, the two (or more) parts of the fixation device also include one or more rigid element, such as rods or flanges for example, which will also span the distance across the divide and serve to further join the parts of the device, particularly against sheer forces (forces that would cause the parts to move relative to one another, either along the divide or into/out of the plane of the fixation device.

Another advantage of the invention in a preferred form is the ability to quickly separate the portions of the device in the event that the bones have to be re-separated post-fixation, as in an emergency procedure. In this form, a simple single cut needs to be made of the joinder element used with the ratchet mechanism, then the parts are movable laterally. To thereafter re-join the still emplaced parts, a new joinder element is used. The ratchet mechanism could be made replaceable to that end (pop-out pop-in), or conceivably could be designed simply to receive a new joinder element.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

While the embodiments described hereinafter are in the environment of an orthopaedic fixation device, system and method for use on the sternum, in particular, it should be appreciated that the disclosure has broader application. That could be, for instance, such as where bone or other body parts having suitable rigidity require closure or other relational organization, such as joining two opposing anatomical structures. This could be in the context of a traumatic break or other unintended separation, or as part of a surgical procedure. Thus, the present disclosure can have usefulness in contexts beyond fixation of bones which have been resected in surgery.

In general, the present disclosure relates to implantable fixation devices for rejoining opposed portions of a separated bone. Implantable is used in the sense that it is sub-cutaneous, but it is possible that applications leaving the fixation device external could be envisioned.

One such device which has been developed according to aspects of the invention in the context of joining two halves of the sternum, includes two corresponding plates that are configured to be aligned and coupled to a bone, such as a sternum, pre-resection of the bone or prior to cutting/separating the bone. The placement of the corresponding plates provides a gap between the edges of the plates that face one another allowing for and guiding a cutting tool for separating the bone. After the bone has been cut and the desired surgical procedure performed, the plates also assist in realigning and fixation of the bone portions. For example, at least one plate may include a ratchet mechanism that is configured to tighten a locking element and draw the two plates together and into alignment with one another.

Note here again, the fixation device could also be emplaced post-resection, although this is considered a less-advantageous use of the device as currently perceived. Also, the parts of the device need not be plates or planar elements, but this shape was considered most-desirable in the environment of a sternal rejoining device and system.

Figure 1:
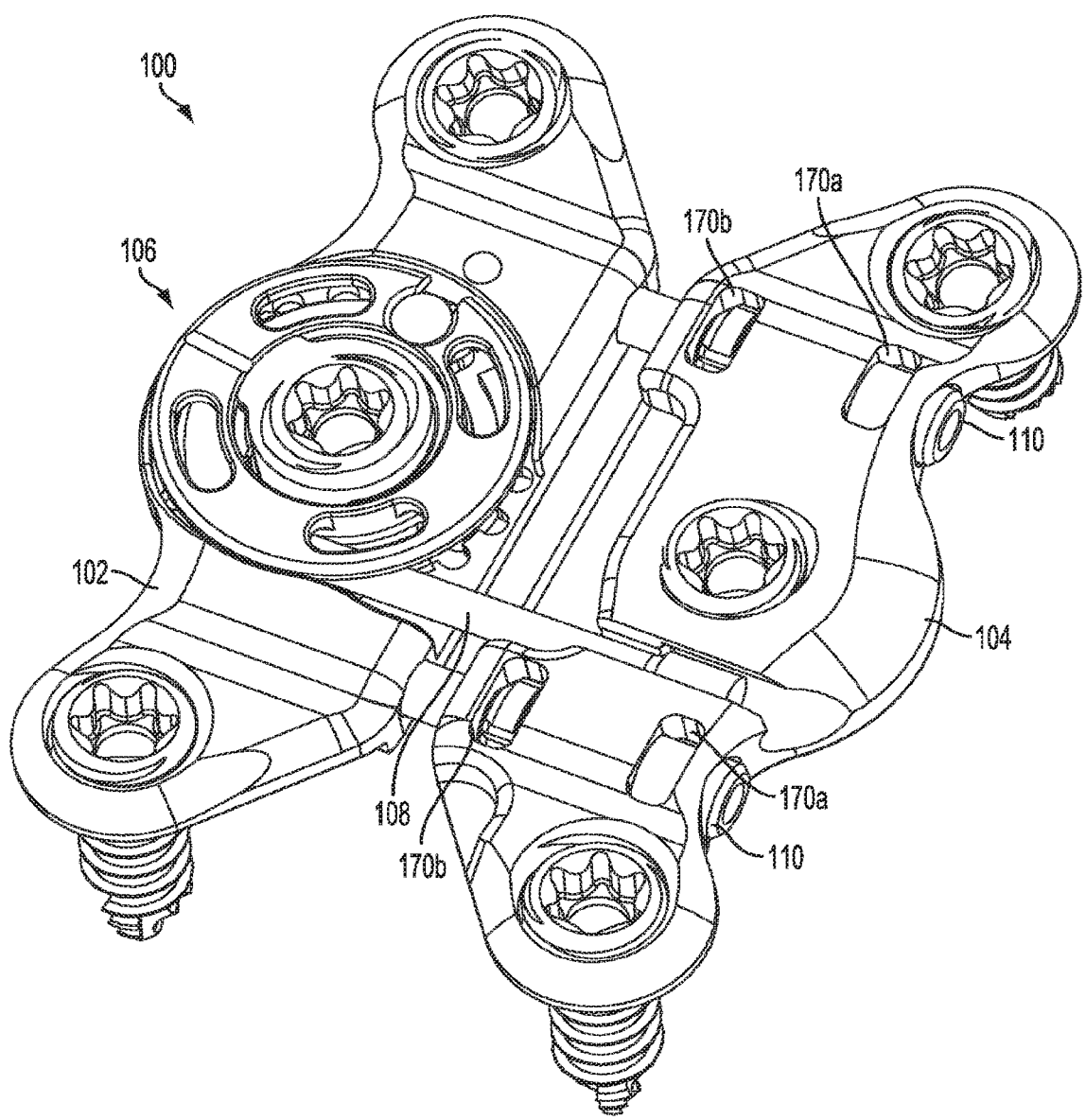
FIG. 1 illustrates a perspective view of an implantable fixation device according to an aspect of the disclosure.

FIGS. 1-5 illustrate an implantable fixation device 100 in the form of two plates according to an embodiment of the disclosure. As illustrated in FIG. 1, the fixation device 100 includes a first plate 102 and a second plate 104. The first plate 102 includes a ratchet mechanism 106 for use in tightening a locking element 108 to pull the first plate 102 and second plate 104 together, as will be more particularly described hereafter. One or more shear pins 110 may be inserted into the second plate 104 to assist in aligning the first plate 102 and second plate 104, and to resist longitudinal and transverse shear forces applied to bone portions post-separation. Other interengaging elements spanning the divide and serving to stabilize the adjacent plates against these forces can be envisioned.

Figure 2:
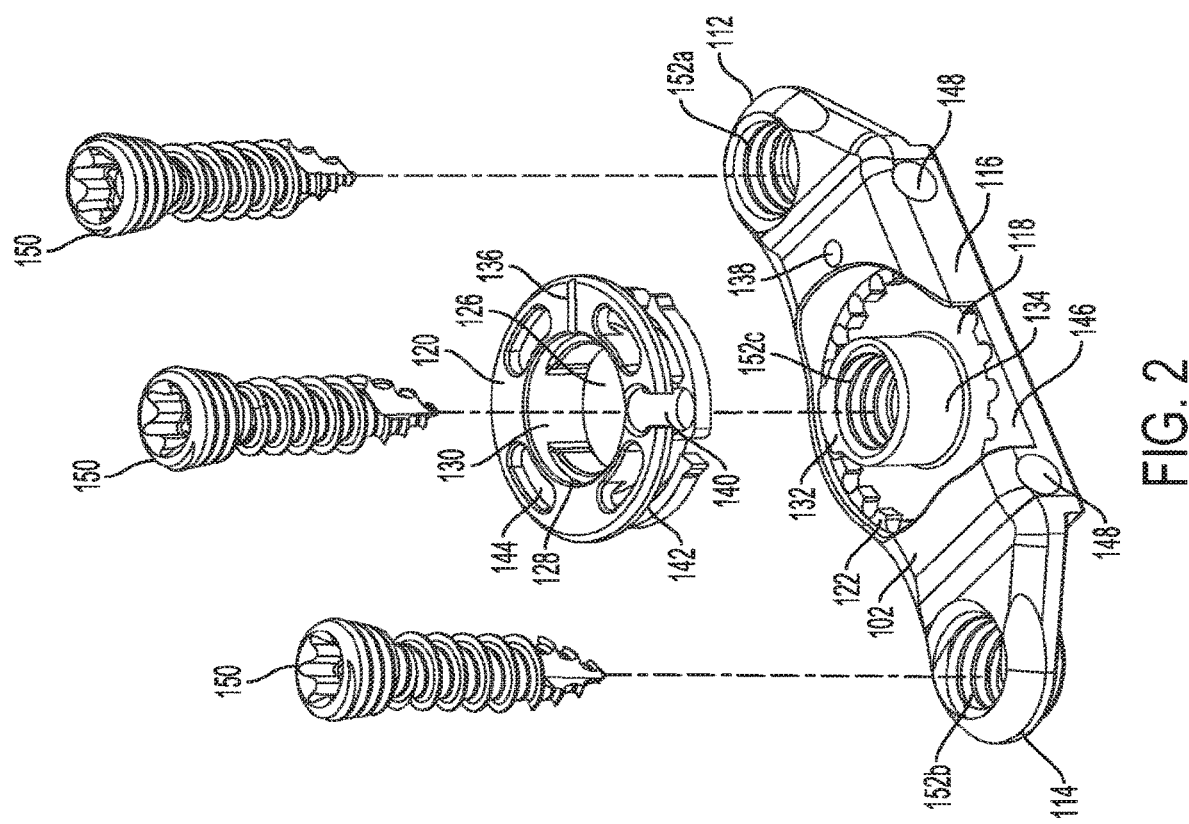
FIG. 2 illustrates an exploded view of a first plate of the implantable fixation device of FIG. 1 according to the disclosure.

Referring to FIG. 2, the first plate 102 includes a first end 112, a second end 114, and a first face 116 configured to be positioned facing a face of the second plate 104, and the ratchet mechanism 106. The ratchet mechanism 106 includes a ratchet recess or well 118 and a ratchet wheel 120. The ratchet recess 118 is located in substantially a central portion of a top portion (i.e., facing away from a body/bone onto which the plate may be attached) of the first plate 102 between the first and second ends 112 and 114. As illustrated, the ratchet recess 118 includes a plurality of teeth 122 around a circumference of the ratchet recess 118 that extend radially inward towards a center of the ratchet recess 118. Other types of ratcheting mechanisms can be envisioned. For instance, rather than a wheel, a post or boss could be used upon which the locking element may be received.

Figure 3:
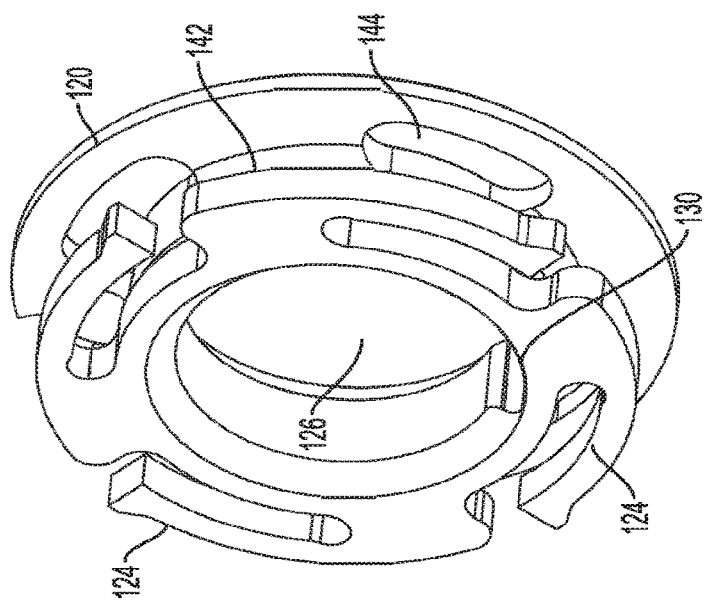
FIG. 3 illustrates a perspective view of a ratchet wheel of the first plate of FIG. 1 according to the disclosure.

The ratchet wheel 120 is removably disposed in the ratchet recess 118. This will be more particularly described with relation to re-entry after an earlier fixation procedure, as for emergency reentry. Referring to FIGS. 2 and 3, the ratchet wheel 120 includes one or more pawls 124 configured to engage the teeth 122 and allow the ratchet wheel to rotate in one direction while preventing rotation in the opposite direction. As illustrated, the ratchet wheel 120 includes four pawls 124 and the ratchet recess 118 includes 20 teeth 122. This provides for a ratchet mechanism that locks, thereby preventing rotation in the opposite direction, at about each eighteen degree increment of rotation. However, it should be appreciated that the number of pawls 124 and teeth 122 may be increased or decreased to provide a ratchet mechanism that locks, thereby preventing rotation in the opposite direction, at any desired degree increment of rotation.

Figure 2C:
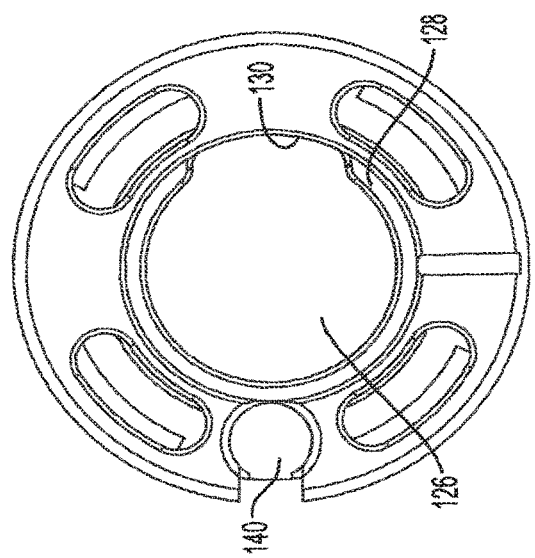
FIGS. 2a through 2c illustrate the ratchet wheel attachment of the device of FIG. 1.
Figure 2A:
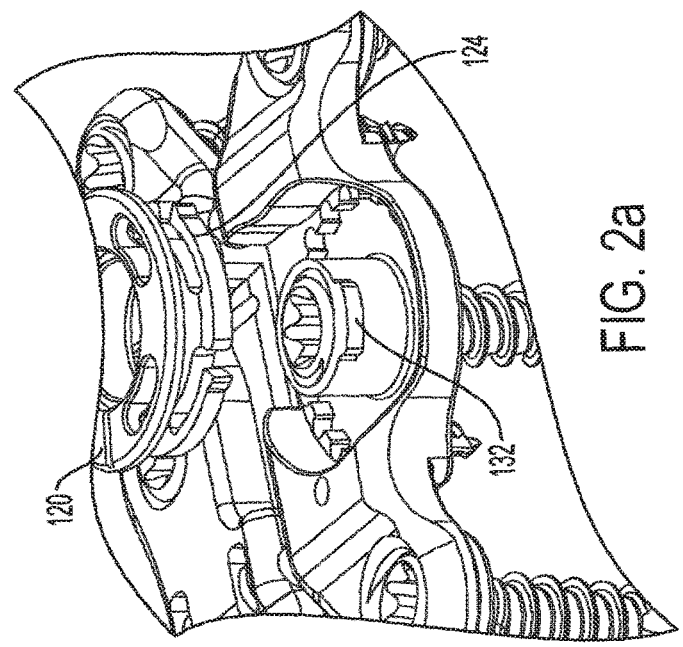
Figure 2B:
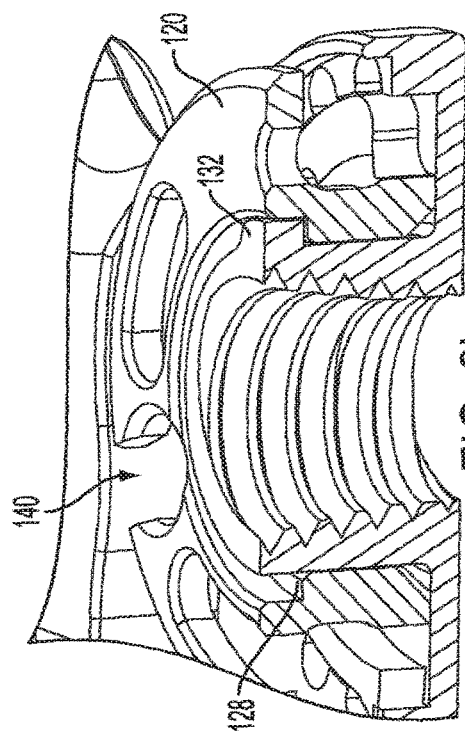

The ratchet wheel 120 also includes an aperture 126 including a ledge 128 extending substantially circumferentially around the aperture 126 and extending radially inward toward a center of the aperture 126. Perhaps best illustrated by reference to FIGS. 2a through 2c, the ratchet wheel attachment utilizes a cut-out or groove area 130 configured to receive a protrusion 132 of a boss 134. The boss 134 extends in an upward direction from a central portion of the ratchet recess 118 and includes the protrusion 132 proximal to a top edge of the boss 134 that extends radially outward from a center of the boss 134. This protrusion and groove 130 arrangement allows for the wheel to be put into place and then held in the well. Once the wheel is advanced, then the protrusion is captured, holding the ratchet wheel 120 in the wheel well, yet readily removable from the ratchet recess 118 if necessary by later realigning the protrusion and groove. One could also envision using a cut-out in the surface which is alignable with the protrusion 132, with the protrusion then riding on the shoulder presented by the surface, once the wheel is rotated to place the protrusion out of alignment. The protrusion could also be a flexible finger, which is pressed inboard when the wheel is being emplace, and then springing outboard onto the shoulder presented by the surface.

When the ratchet wheel 120 is installed in the ratchet recess 118, the boss 134 extends into the aperture 126 of the ratchet wheel 120 and the protrusion 132 extends over the ledge 128 to prevent the ratchet wheel 120 from accidentally being removed from the ratchet recess 118.

To facilitate ease of assembly and disassembly, the ratchet wheel 120 may include an indicator 136 and the first plate 102 may include a corresponding indicator 138, that when aligned indicate that the cut-out is aligned with the protrusion 132. This allows a use to visually identify the correct position of the ratchet wheel 120 with respect to the first plate 102 to install or remove the ratchet wheel 120 from the first plate 102.

The ratchet wheel 120 also includes a locking element capture receptacle 140 and an annular channel 142. The locking element capture receptacle 140 is configured to receive an end of the locking element 108 (illustrated in FIG. 1). The channel 142 is configured to receive and allow the locking element 108 (illustrated in FIG. 1) to be coiled around the ratchet wheel 120 to tighten the locking element 108 (illustrated in FIG. 1), as described in further detail hereinafter.

The ratchet wheel 120 may also include one or more tool engaging features 144, illustrated as oblong apertures. The tool engaging features 144 are configured to receive a corresponding male feature of a tool for use in rotating the ratchet wheel 120 to coil the locking element 108 (illustrated in FIG. 1) around the ratchet wheel 120.

In another embodiment, the ratchet wheel 120 may be shaped to be received in a drive receptacle of a tool. For example, referring to FIGS. 9 and 10, a top portion of ratchet wheel 120' may be configured to be received and engaged by a drive receptacle of a tool for use in rotating the ratchet wheel 120' to coil the locking element 108 around the ratchet wheel 120'.

Referring to FIG. 2, the first plate 102 includes a cut-out or area of reduced wall height 146 proximal to the face 116. This allows the locking element 108 (illustrated in FIG. 1) to extend from the first plate 102 and be coupled to the second plate 104, as described in further detail hereinafter.

The first plate 102 may include one or more shear pin receiving receptacles 148 in the face 116. The receiving receptacles 148 are configured to receive corresponding shear pins 110 (illustrated in FIG. 1) extending from the second plate 104. This assists in aligning the first and second plates 102 and 104 when the implantable fixation device 100 is installed and used. While pins are described to this end in this particular embodiment, other collateral engaging pieces or portions can be envisioned. Overlying flanges, tongue-and-groove mating parts, press-in spanning members and so forth could be applied. Pins are disclosed in this embodiment, as easily manipulated to snugly engage across the divide and between the two plate parts.

The first plate may also include one or more threaded fastener apertures configured to receive corresponding fasteners 150 to couple the first plate 102 to a bone or other body part. As illustrated in FIG. 2, the threaded fastener apertures include a first aperture 152a positioned proximal to the first end 112, a second aperture 152b positioned proximal to the second end 114, and a third aperture 152c in the boss 134. The apertures 152a-c may have a circular shape, oblique shape, or other shape, or a combination thereof. For example, the first and second apertures 152a and 152b may be oblique and the third aperture 152c may be circular. While there are three fasteners 150 and three corresponding threaded fastener apertures 152a-c, there may be more or less than three in the first plate 102 and the fasteners may be screws, pins, rivets, or other types of fasteners, etc.

Figure 4:
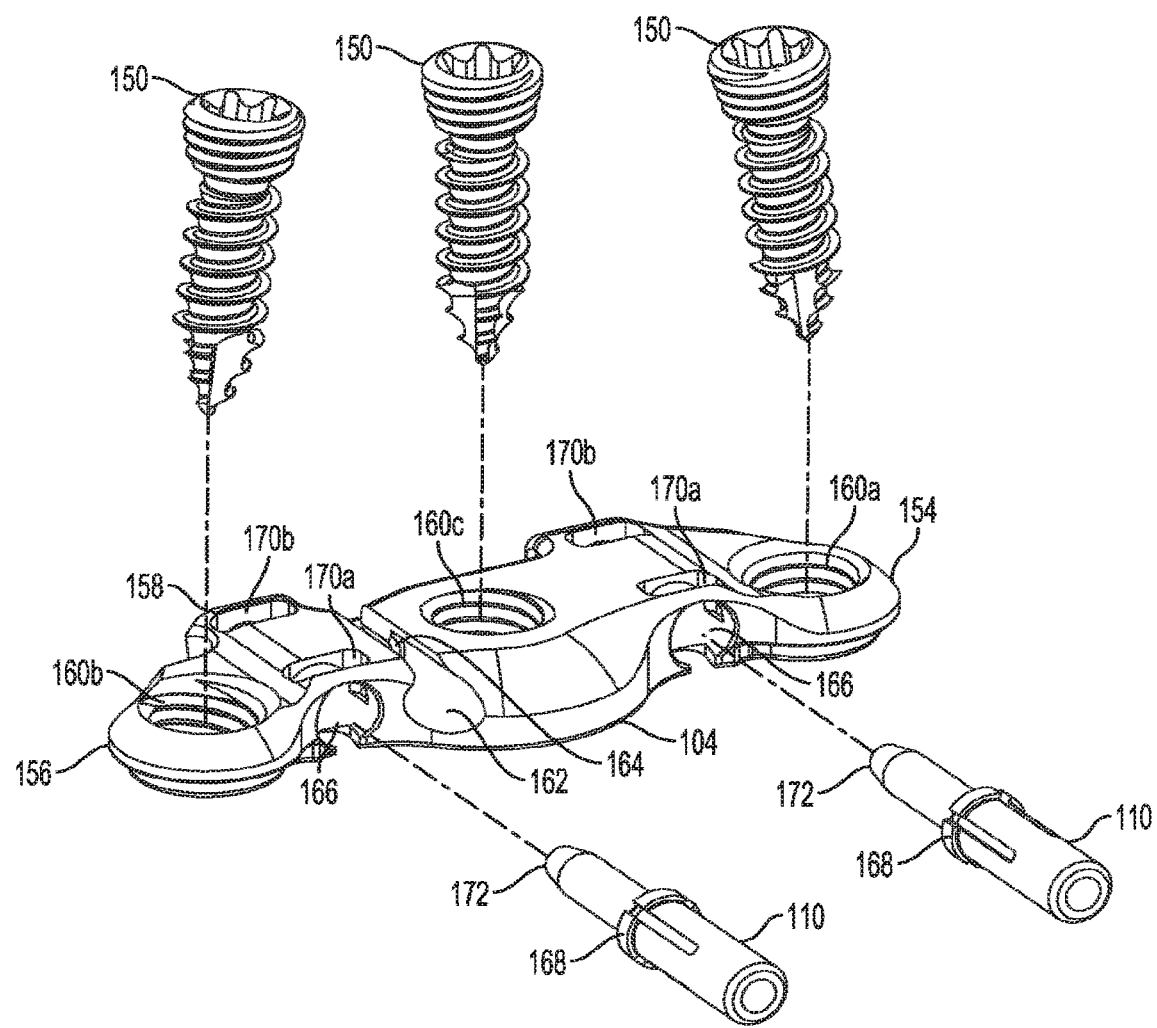
FIG. 4 illustrates an exploded view of a second plate of the implantable fixation device of FIG. 1 according to the disclosure.

Referring to FIG. 4, the second plate 104 includes a first end 154, a second end 156, and a second face 158 configured to be positioned facing the first face 116 of the first plate 102 (illustrated in FIG. 2) in an opposed relationship. Similar to the first plate 102, the second plate 104 may include one or more threaded fastener apertures configured to receive corresponding fasteners 150 to couple the second plate 104 to a bone or other body part. As illustrated in FIG. 4, the threaded fastener apertures include a first aperture 160a positioned proximal to the first end 154, a second aperture 160b positioned proximal to the second end 156, and a third aperture 160c substantially in a center of the second plate 104. The apertures 160a-c may have a circular shape, oblique shape, or other shape, or a combination thereof. For example, the first and second apertures 160a and 160b may be oblique and the third aperture 160c may be circular. While there are three fasteners 150 and three corresponding threaded fastener apertures 160a-c, there may be more or less than three in the second plate 104 and the fasteners may be screws, pins, rivets, or other types of fasteners, etc.

The second plate 104 may also include a locking element capture channel 162 formed in a top of the second plate 104 and extending across the second plate 104 in a substantially perpendicular direction to a longitudinal axis of the second plate 104. The locking element capture channel 162 is configured to receive an end of the locking element 108 (illustrated in FIG. 1), as described in further detail hereinafter. The locking element capture channel 162 may also include a stop or ledge 164 configured to prevent the locking element 108 (illustrated in FIG. 1) from being pulled out of the channel in a direction of the face 158.

As illustrated in FIG. 4, one or more apertures 166 extend through the second plate 104 in a substantially perpendicular direction to the longitudinal axis of the second plate 104. The apertures 166 are configured to receive corresponding shear pins 110. One aperture 166 may be positioned between the first aperture 160a and the third aperture 160c, and located to align with one of the receiving receptacles 148 of the first plate 102 (illustrated in FIG. 2). Another aperture 166 may be positioned between the second aperture 160b and the third aperture 160c, and located to align with the other of the receiving receptacles 148 of the first plate 102 (illustrated in FIG. 2).

The shear pins 110 may include deflectable prongs 168 and the second plate may include corresponding prong receiving receptacles configured to receive the prongs 168 to hold the shear pins 110 in the second plate 104. As illustrated in FIGS. 1 and 4, the second plate 104 includes first prong receiving receptacles 170a and second prong receiving receptacles 170b. Each first prong receiving receptacle 170a communicates with a corresponding one of the apertures 166, and is located toward the entry point on the second plate. Similarly, each second prong receiving receptacle 170b communicates with a corresponding one of the apertures 166, and is located on the other side of the second plate.

Figure 7:
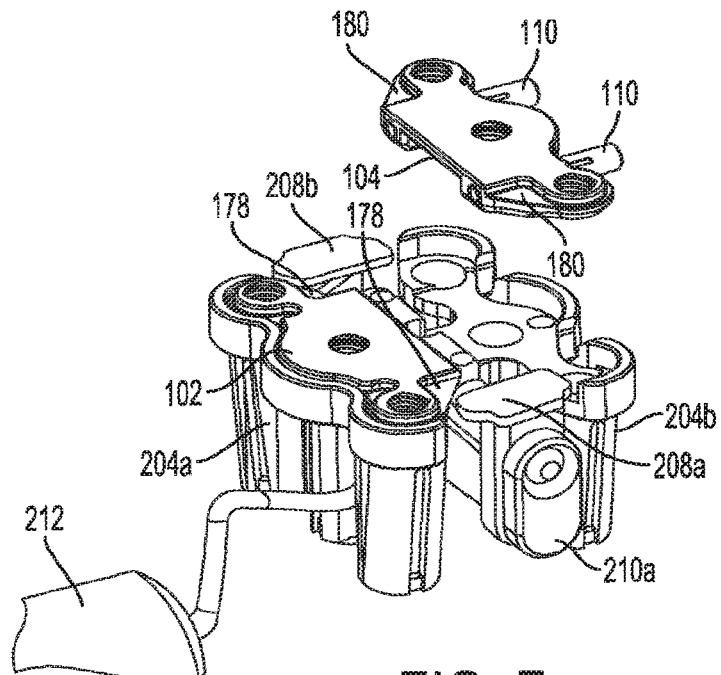
FIG. 7 illustrates the first and second plates being installed in the fixation device positioning holder according to the disclosure.

Referring to FIGS. 4 and 7, the first prong receiving receptacles 170a correspond to a first position of the shear pins 110 (as illustrated in FIG. 7). In the first position, the deflectable prongs 168 of the shear pins 110 are engaged with the first prong receiving receptacles 170a. In this position, ends 172 of the shear pins 110 are positioned within the apertures 166 and do not extend past the face 158 of the second plate 104.

Figure 5:
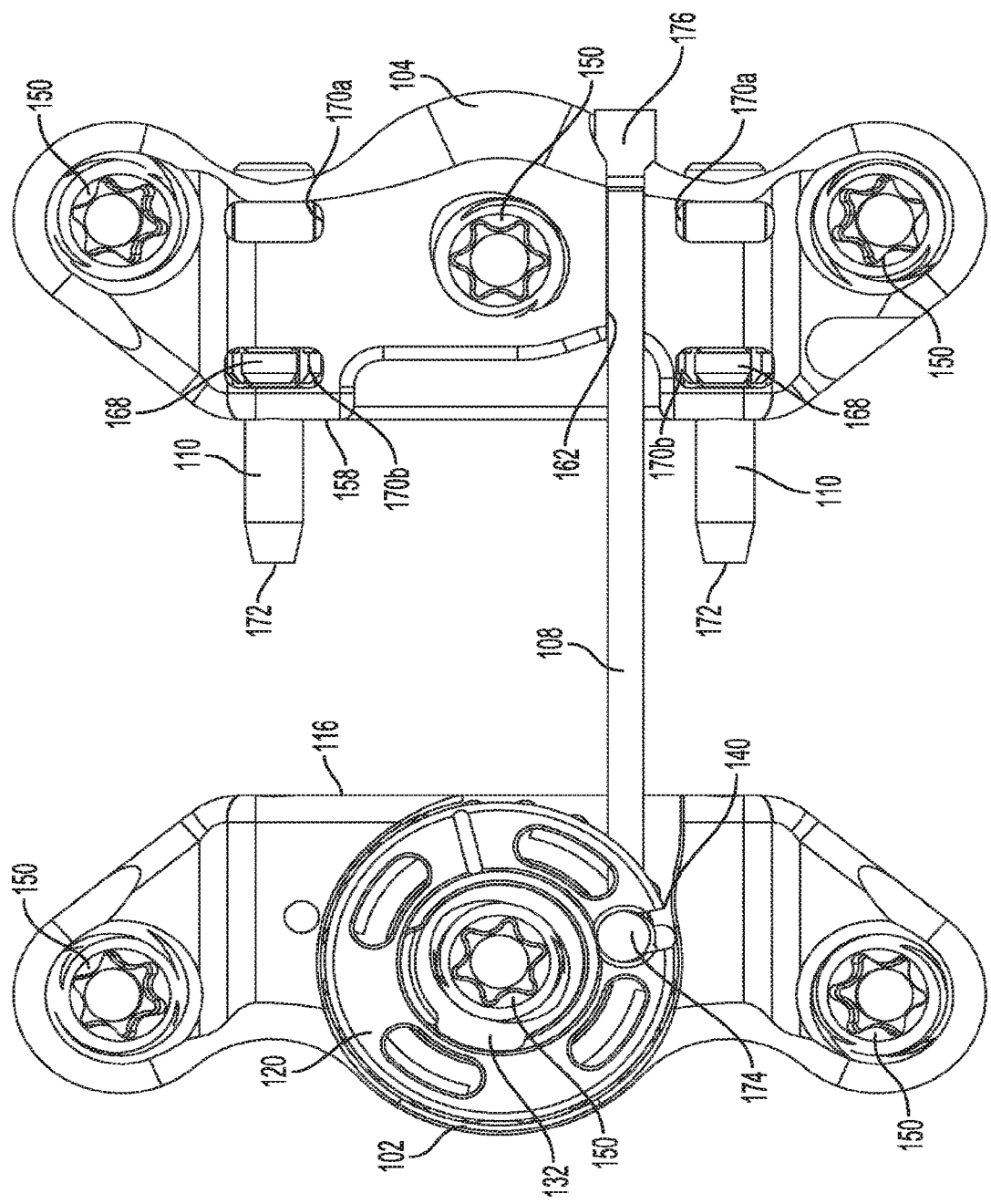
FIG. 5 illustrates the first and second plates aligned in a first position.

Referring to FIGS. 4 and 5, the second prong receiving receptacles 170b correspond to a second position of the shear pins 110 (as illustrated in FIG. 5). In the second position, the deflectable prongs 168 of the shear pins 110 are engaged with the second prong receiving receptacles 170b. In this position, the ends 172 of the shear pins 110 extend past the face 158 of the second plate 104, and extend into the receiving receptacles 148 in the face 116 of the first plate 102 (illustrated in FIG. 2) when the implantable fixation device 100 is installed and used to hold two corresponding bone portions together.

Referring to FIG. 5, the locking element 108 may be a bendable rod and have a first end 174 and a second end 176. The first end 174 may include a first engagement portion that extends substantially perpendicular to a longitudinal axis of the locking element 108. The first end 174 may be installed in the locking element capture receptacle 140 of the ratchet wheel 120. The second end 176 may include a second engagement portion having a diameter greater than a remainder of the locking element 108. The second end 176 may be installed in the locking element capture channel 162 of the second plate 104. The locking element could take other forms, such as a sturdy wire or the like. Conceptually, it is an elongate member that is capable of being wound upon the ratchet wheel.

When the locking element 108 is installed and the ratchet wheel 120 is rotated, the locking element 108 is coiled around the ratchet wheel 120 to urge the first plate 102 and second plate 104 together and into alignment with one another. In this respect, the second end 176 may contact the stop or ledge 164 of the locking element capture channel 162 and allow the first plate 102 and second plate 104 to be pulled together.

Figure 6:
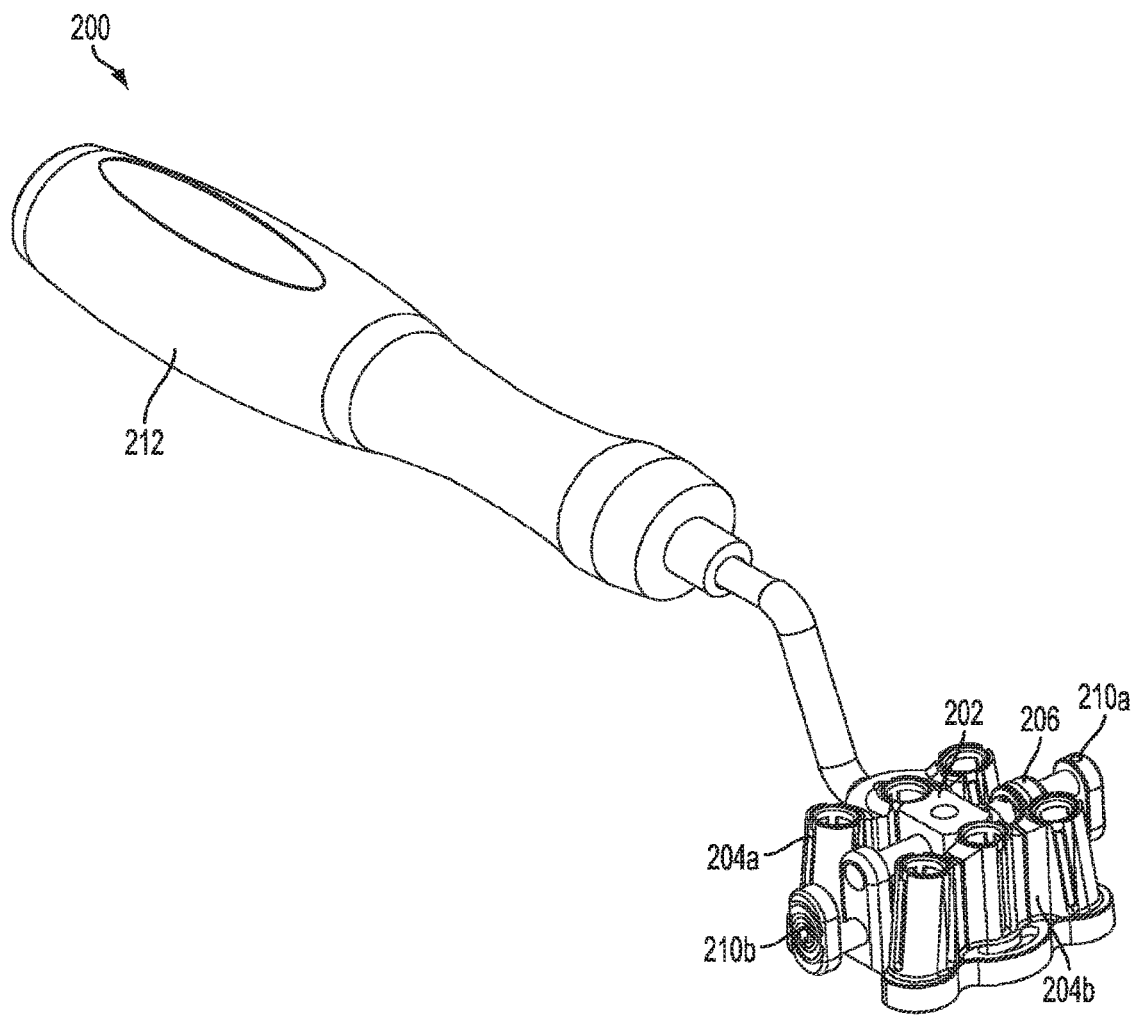
FIG. 6 illustrates a fixation device positioning holder according to the disclosure.
Figure 8:
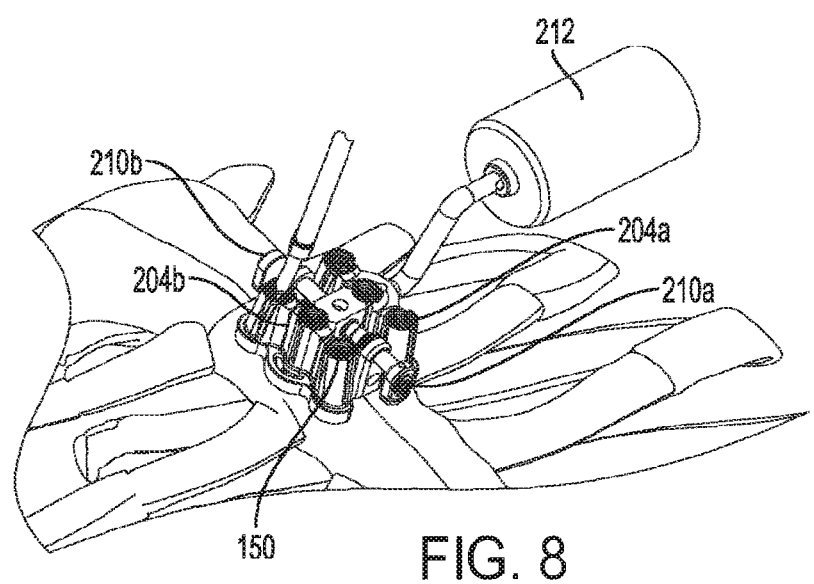
FIG. 8 illustrates the first and second plates being affixed to a bone according to the disclosure.

The first plate 102 and second plate 104 may be configured to be used in conjunction with a fixation device positioning holder. Referring to FIGS. 6-8, the positioning holder 200 includes a body 202 including a first set of fastener guides 204a and a second set of fastener guides 204b on opposite sides of the body 202, a compression attachment mechanism 206, and attachment feet 208a and 208b. A version of a positioning holder is disclosed in U.S. Ser. No. 62/039,672, the disclosure of which is incorporated herein by reference, and to which priority is claimed. Note that the present invention is not to be limited to such a positioning holder, but could be emplaced using markings made by a template or the like for the fixation element locations.

The first and second sets of fastener guides 204a and 204b provide a housing to guide fasteners 150 for insertion into the threaded fastener apertures 152a-c of the first plate 102 (illustrated in FIG. 2) and the threaded fastener apertures 160a-c of the second plate 104 (illustrated in FIG. 4). Each of the first and second sets of fastener guides 204a and 204b may include cylindrical hollow tube like guide barrels that are positioned and oriented to align with the threaded fastener apertures 152a-c of the first plate 102 (illustrated in FIG. 2) and the threaded fastener apertures 160a-c of the second plate 104 (illustrated in FIG. 4). The positioning holder 200 may also be used to guide a driver and/or drill depending on the application, and/or to guide other instruments, for example, to place markings, pegs, headless pins, screws, etc. in a bone.

The compression attachment mechanism 206 may include a spring loaded mechanism that when compressed causes a distance between the attachment feet 208a and 208b to increase and when released causes the distance between the attachment feet 208a and 208b to decrease and mate with corresponding recesses 178 in the first plate 102 and corresponding recesses 180 in the second plate 104.

The attachment feet 208a and 208b serve to hold the first and second plates 102 and 104 in the positioning holder 200 at a predetermined distance from each other. As illustrated in FIG. 7, the attachment feet 208a and 208b hold the first and second plates 102 and 104 in a coplanar arrangement, with the threaded fastener apertures 152a-c of the first plate 102 (illustrated in FIG. 2) aligned with the respective guide barrels of the first set of fastener guides 204a and the threaded fastener apertures 160a-c of the second plate 104 (illustrated in FIG. 4) aligned with the respective guide barrels of the second set of fastener guides 204b.

The compression attachment mechanism 206 allows for the positioning holder 200 to be coupled to and uncoupled from the first and second plates 102 and 104 quickly and easily, simply by compressing the spring loaded mechanism. For example, when gripping portions 210a and 210b are compressed, the distance between the feet 208a and 208b is increased. This allows the first and second plates 102 and 104 to be placed in the positioning holder 200, and when the compression force applied to the gripping portions 210a and 210b is released, the distance between the feet 208a and 208b decreases and the feet 208a and 208b mate with the recesses 178 and 180 of the first and second plates 102 and 104, respectively.

The positioning holder 200 may include a handle 212 coupled to the fixation device 100 for ease of assembly of elements and placement of the plates (such as the plates 102 and 104). The handle 212 may have an ergonomic design for comfort and control of the positioning holder 200. The handle 212 may also be angled to accommodate soft tissues and various surgical approaches.

The positioning holder 200 may also include one or more spikes (not shown) extending from a bottom of the positioning holder 200 to assist in placing and holding the positioning holder 200 and the first and second plates 102 and 104 in a proper orientation as the fasteners 150 are driven to couple the first and second plates 102 and 104 to a bone or other portion of a patient's body.

In an embodiment, the first and second plates 102 and 104 may be used in a sternal resection procedure (or some other type of bone cut, where the bones are to be placed back into a desired juxtaposition). For example, referring to FIG. 9, soft tissue may be dissected from a surface of the sternum to allow for complete visualization of the bone, illustrated as block 902. In addition to dissecting the soft tissue from the sternum, bony calluses, if present, may also be removed from the midline and sternal surface to allow for proper anatomical reduction and plate placement.

Figure 9:
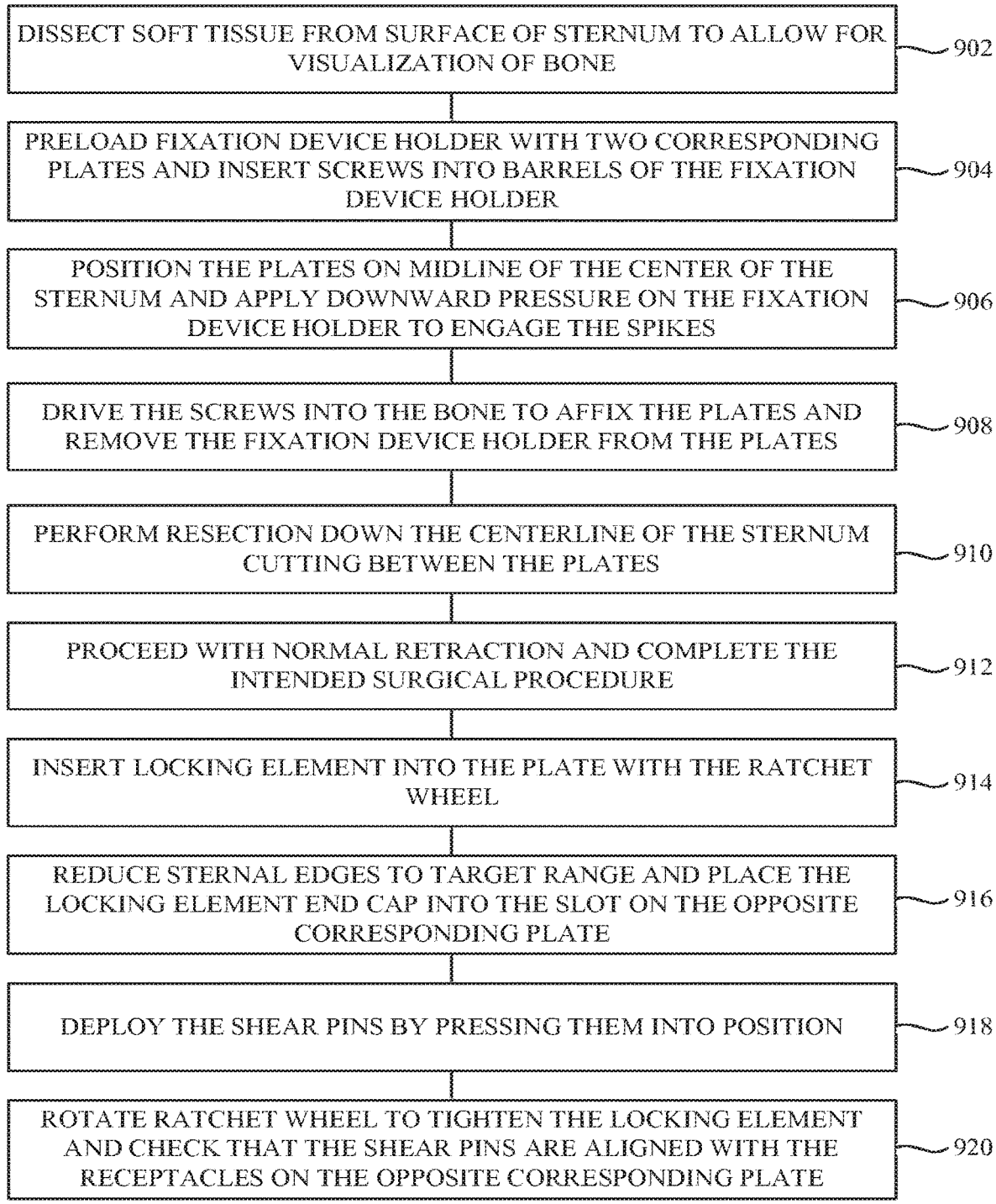
FIG. 9 is a block flow diagram of a method of installing and using the implantable fixation device according to the disclosure.

Referring to FIGS. 7 and 9, the first and second plates 102 and 104 may be loaded into the positioning holder 200, and the fasteners 150 may be inserted into the first and second sets of fastener guides 204a and 204b, illustrated as block 904. Referring to FIGS. 8 and 9, using the handle 212 the first and second plates 102 and 104 are positioned on a midline of a center of a sternum, illustrated as block 906. Once the target position is achieved, gentle downward pressure on the positioning holder 200 may be applied to engage the periosteal spikes of the positioning holder 200 to stabilize the position of the first and second plates 102 and 104 on the sternum.

The fasteners 150 may then be driven into the bone of the sternum using a tool, such as a bone drill, illustrated as block 908. It should be appreciated that if dense cortical bone is present, utilization of a pre-drilled hole may be advisable. Once the fasteners 150 are driven, the gripping portions 210a and 210b are compressed to disengage the attachment feet 208a and 208b from the first and second plates 102 and 104 and remove the positioning holder 200, illustrated as block 908. Depending on the length of resection, more than one implantable fixation device 100 may be installed by repeating the steps described herein.

Figure 10:
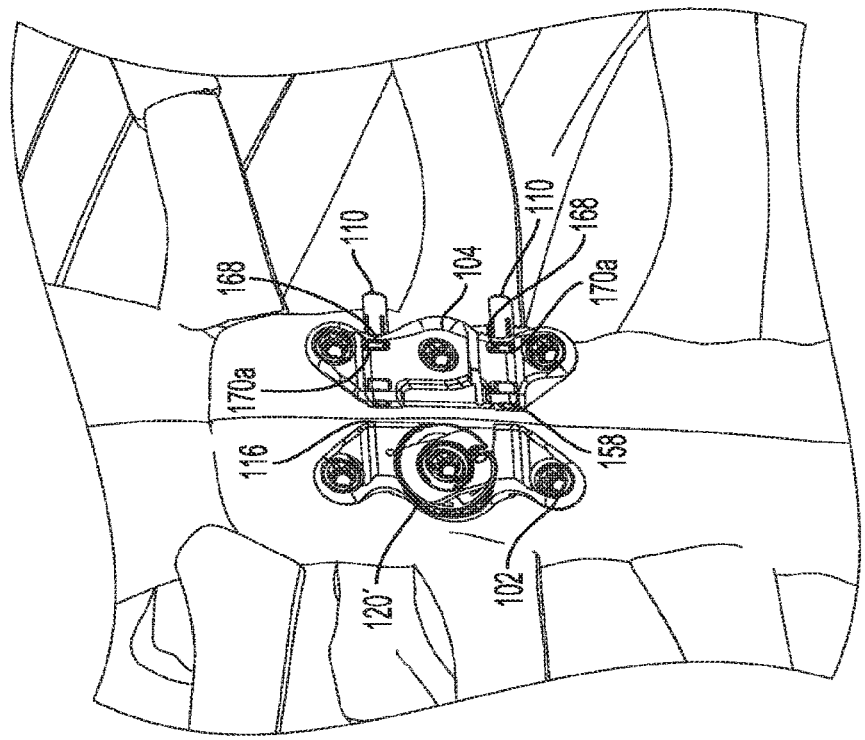
FIG. 10 illustrates the first and second plates of FIG. 1 aligned and oriented in a pre-resection position according to the disclosure.

Referring to FIGS. 9 and 10, sternal resection may then be performed. The first and second plates 102 and 104 are installed with a gap between the faces 116 and 158 of the respective first and second plates 102 and 104. Additionally, the first and second plates 102 and 104 are initially installed with the locking element 108 (illustrated in FIG. 5) removed, and the shear pins 110 are in the first position (i.e., the deflectable prongs 168 are engaged with the first prong receiving receptacles 170a).

A cutting tool may be used to cut the sternum between the first and second plates 102 and 104, using the first and second plates 102 and 104 as a guide, illustrated as block 910. The sternum may then be retracted and a surgical procedure performed, illustrated as block 912.

Figure 11:
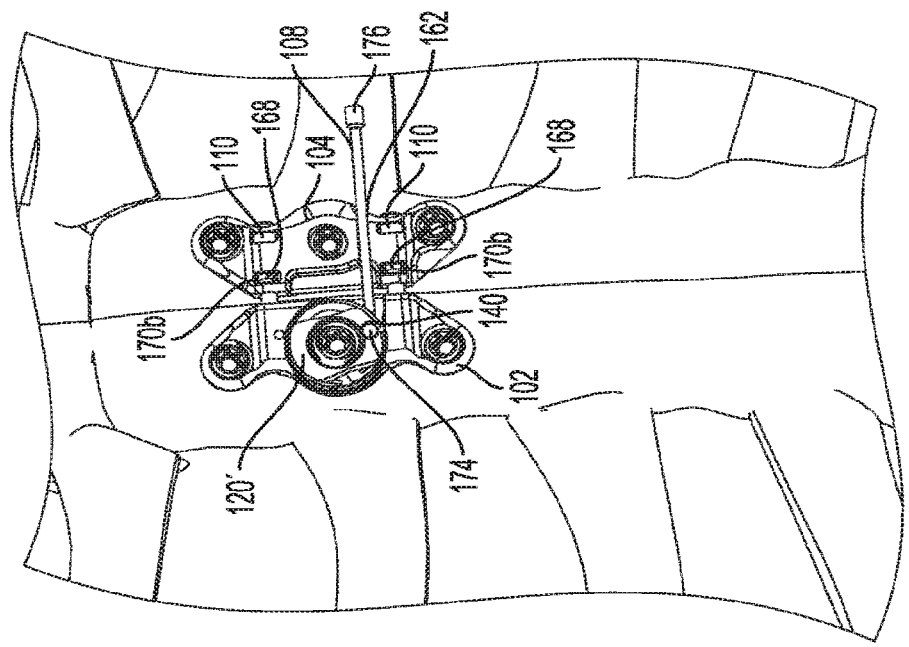
FIG. 11 illustrates the first and second plates of FIG. 1 aligned and oriented in a first post-resection position prior to operation of a ratchet mechanism according to the disclosure.
Figure 12:
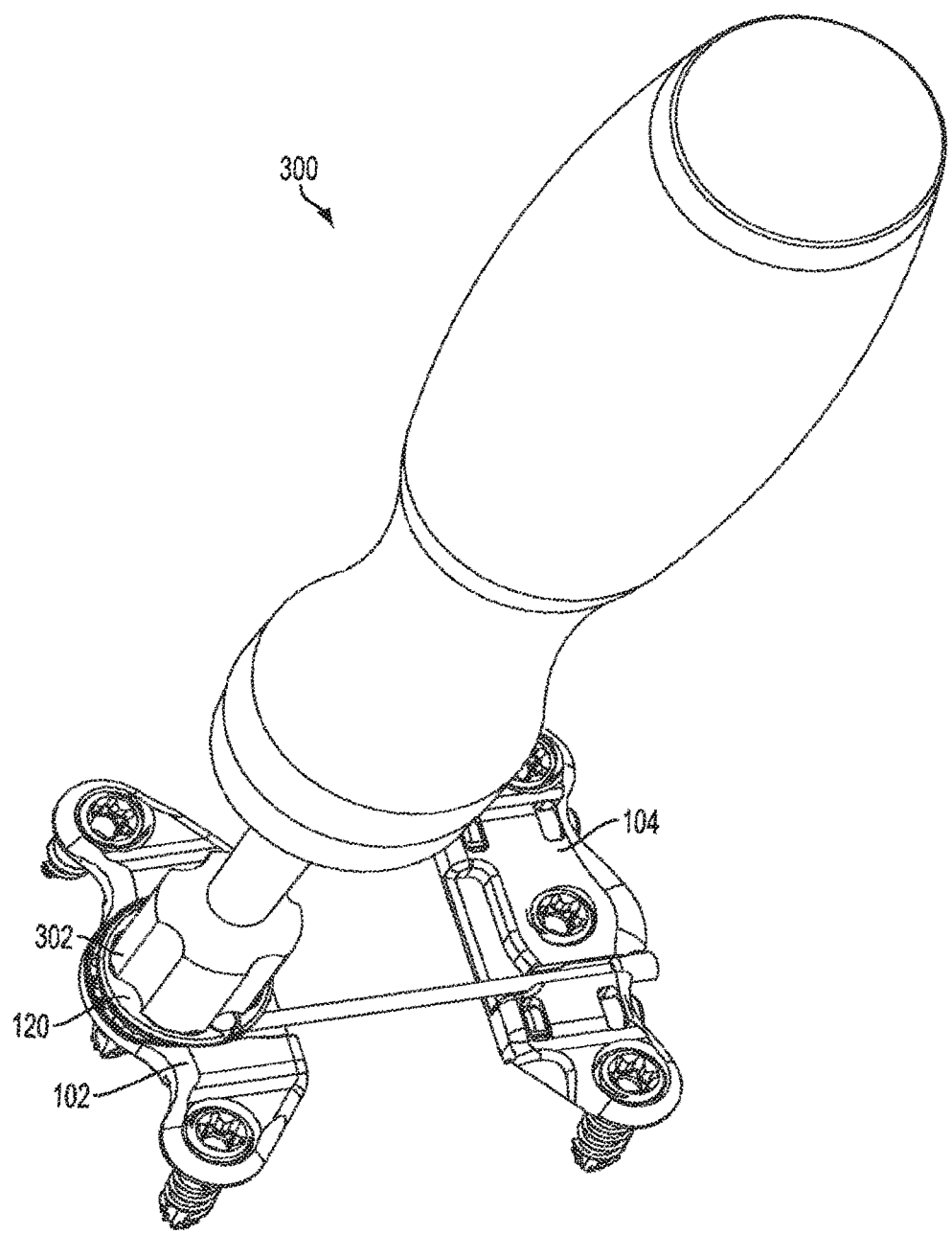
FIG. 12 illustrates a tool for operating a ratchet wheel of the first plate according to the disclosure.

Referring to FIGS. 9 and 11, after the surgical procedure is complete, the first end 174 of the locking element 108 is seated in the locking element capture receptacle 140 of the ratchet wheel 120', illustrated as block 914. The cut portions of the sternum may be reduced back together and the second end 176 is seated in the locking element capture channel 162 of the second plate 104, illustrated as block 916. The ratchet wheel 120' is rotated and the locking element 108 is coiled around the ratchet wheel 120' to urge the first plate 102 and second plate 104 together and into alignment with one another. The ratchet wheel 120' or 120 may be rotated, for example, using tool 300 illustrated in FIG. 12. In an embodiment, the tool 300 includes a driving end 302 having male protrusions that engage the tool engaging features 144 of the ratchet wheel 120.

Figure 13:
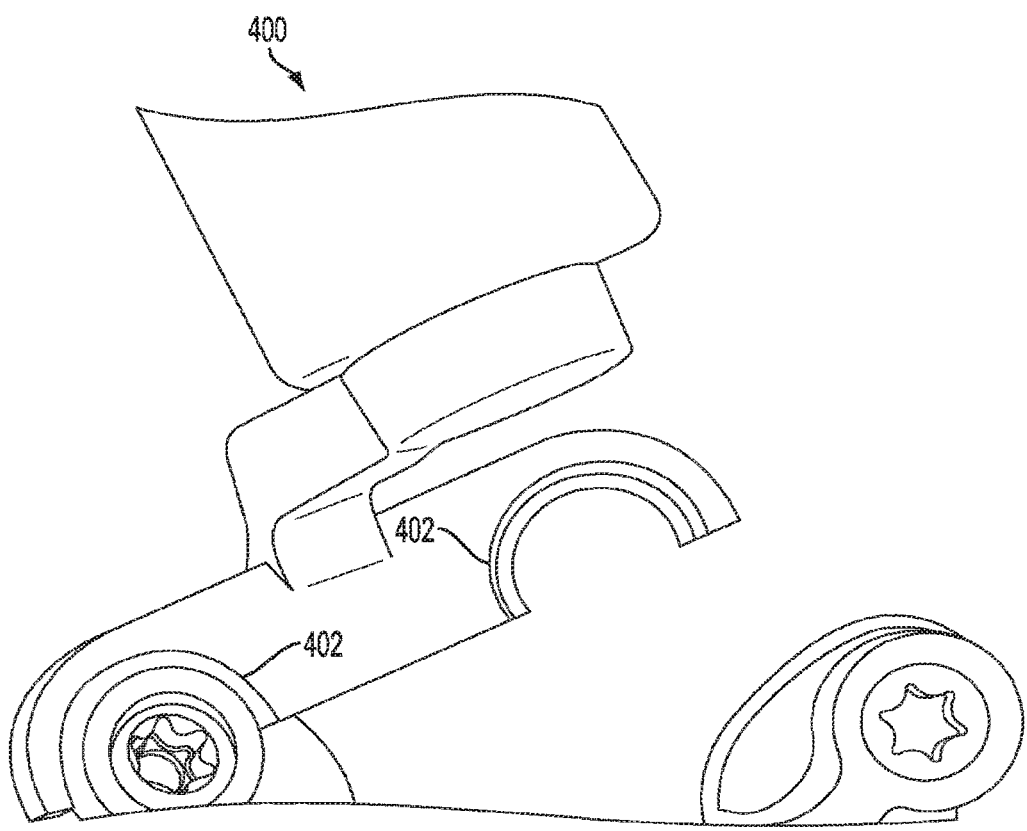
FIG. 13 illustrates a reduction tool for aligning and holding the first and second plates post-resection according to the disclosure.

Gross sternum reduction may be achieved using normal methods including manual external pressure, retraction instruments, wires, etc. Referring to FIG. 13, a reduction/alignment tool 400 may be used to bring the sternal edges into close apposition. As illustrated, the tool 400 includes plate engaging receptacles 402 configured to engage the first ends 112 and 154 or second ends 114 and 156 of the first and second plates 102 and 104, respectively, to hold and align the first and second plates 102 and 104. For example, the first ends 112 and 154 of the first and second plates 102 and 104, respectively, into the plate engaging receptacles 402 and a medial force may be applied on the instrument to bring the sternal edges closer together.

Figure 14:
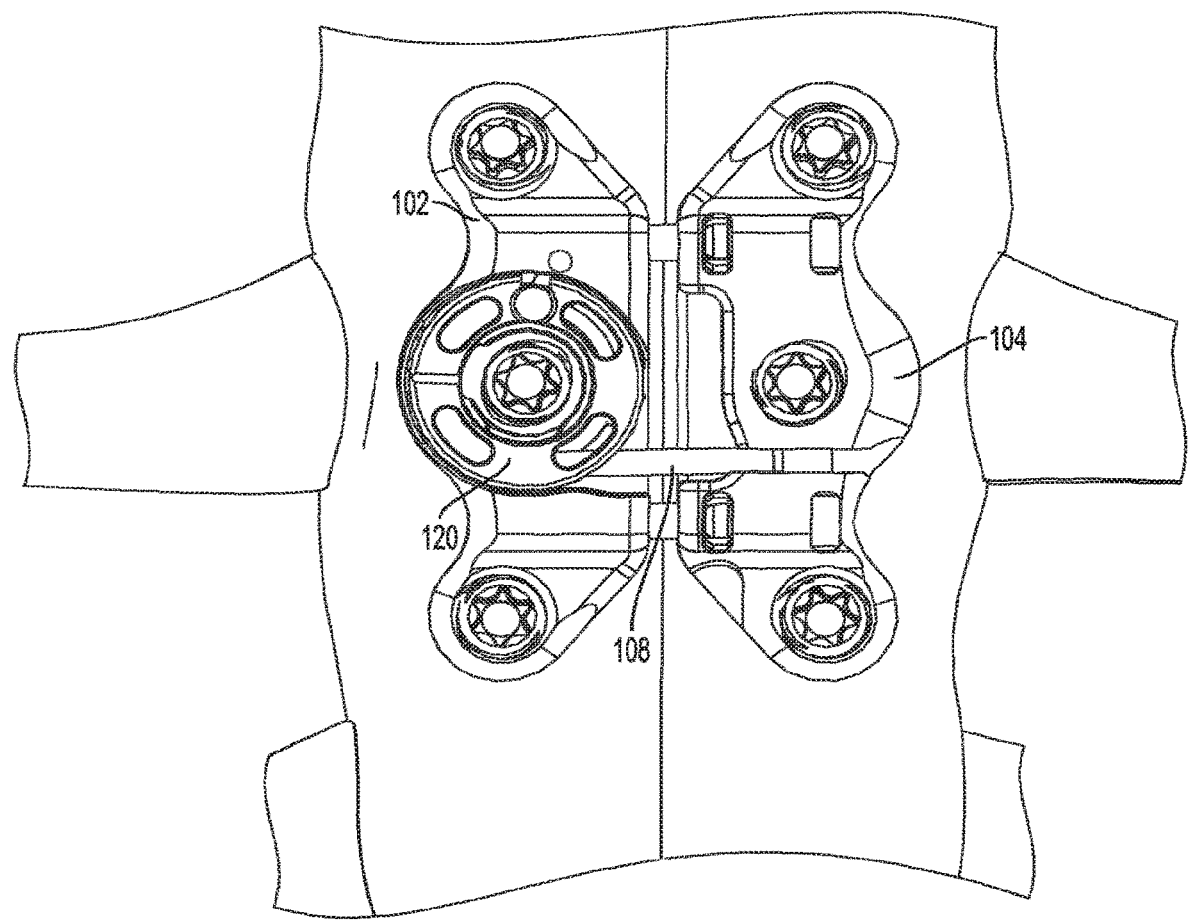
FIG. 14 illustrates the first and second plates of FIG. 1 post-resection according to the disclosure.

Referring back to FIGS. 9 and 11, the shear pins 110 may also be deployed to the second position by pressing them into the second plate 104 in a direction of the first plate 102, illustrated as block 918. This causes the deflectable prongs 168 of the shear pins 110 to engage the second prong receiving receptacles 170b. Referring to FIGS. 9 and 14, final approximation of the sternum is achieved by rotating the ratchet wheel 120 to cause the locking element 108 to be coiled around the ratchet wheel 120. A series of audible clicks may occur as the ratchet wheel 120 is rotated. The sternal edges will be drawn closer into apposition with each click of the ratchet wheel 120, illustrated as block 920.

During the final approximation, it should be ensured that the shear pins 110 are aligned with the receiving receptacles 148 in the face 116 (illustrated in FIG. 2) of the first plate 102, illustrated as block 920. Use of the reduction/alignment tool 400 may be helpful in achieving alignment. As the first and second plates 102 and 104 are brought closer together, the shear pins 110 extend into the receiving receptacles 148 in the face 116 (illustrated in FIG. 2) of the first plate 102. The receiving receptacles 148 may have a depth configured to allow the ends 172 (illustrated in FIG. 4) of the shear pins 110 to contact a bottom of the receiving receptacles 148 (illustrated in FIG. 2) to maintain the first and second plates 102 and 104 with the gap (described above) between them upon final approximation of the sternum. Note that in a preferred form, the shear pins do not "bottom" even if the plates were to touch, so as to ensure that the adjacent bone parts will contact one another.

Figure 15:
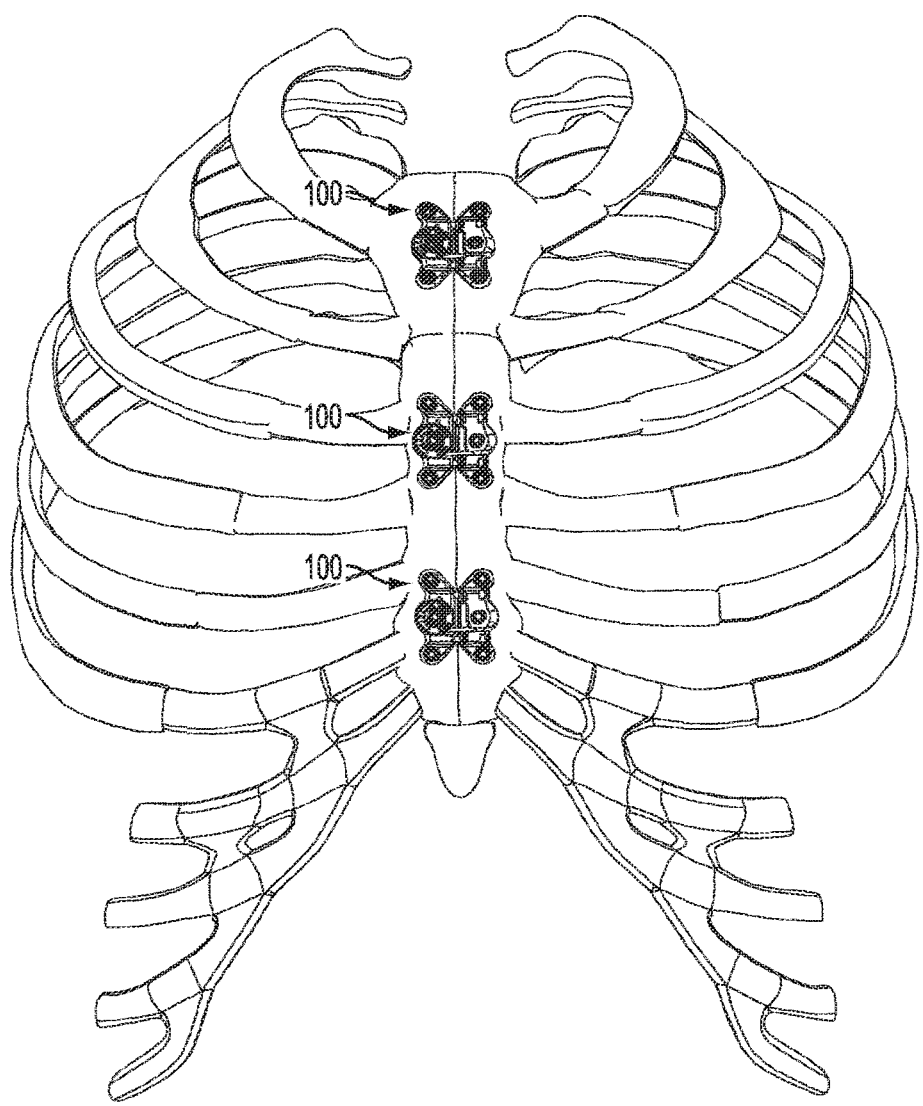
FIG. 15 illustrates a plurality of first and second plates post-resection as they might be located according to the disclosure.
Figure 16:
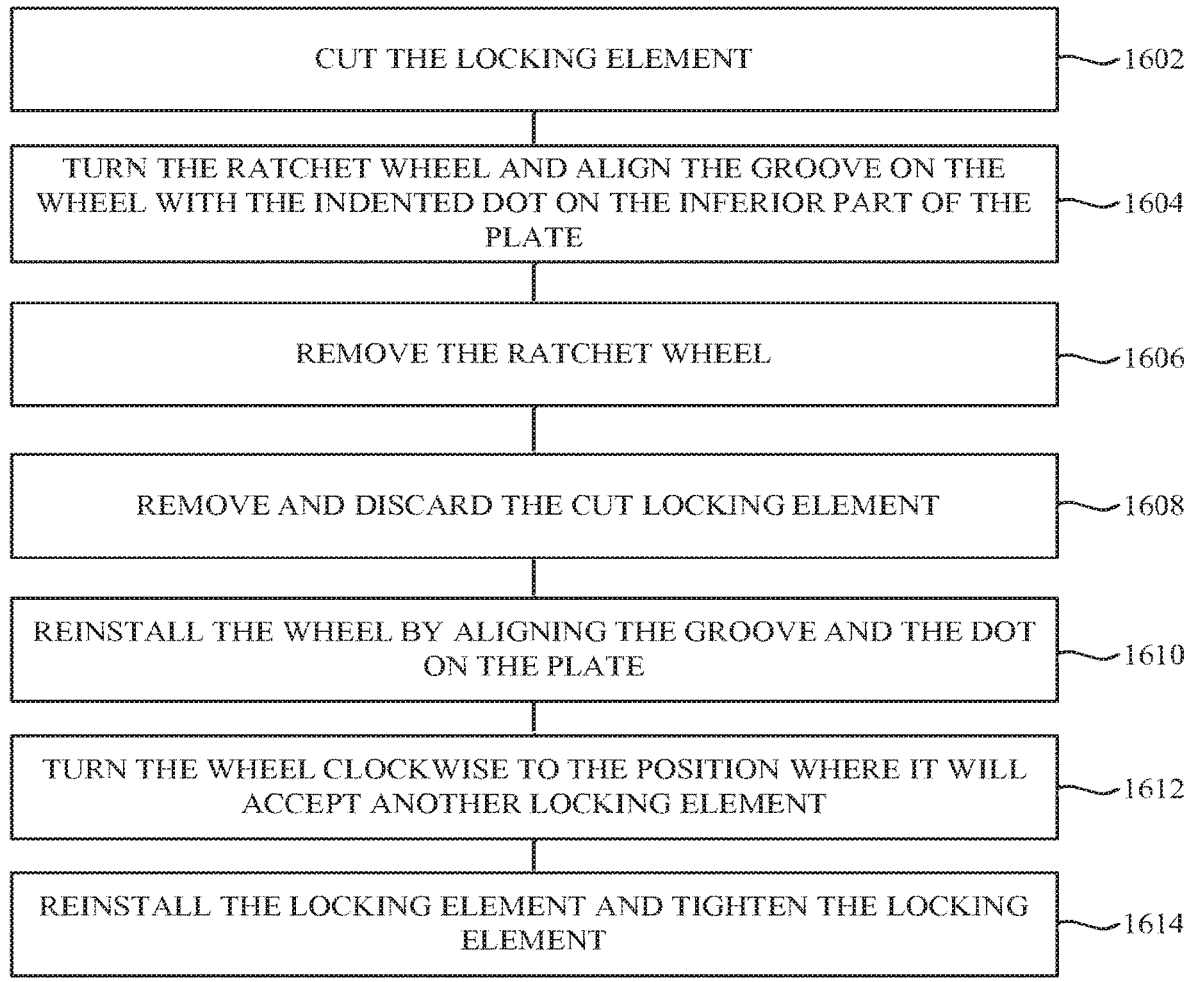
FIG. 16 is a block flow diagram of a method of using the implantable fixation device for reentry/re-resection of the bone according to the disclosure.
Figure 17:
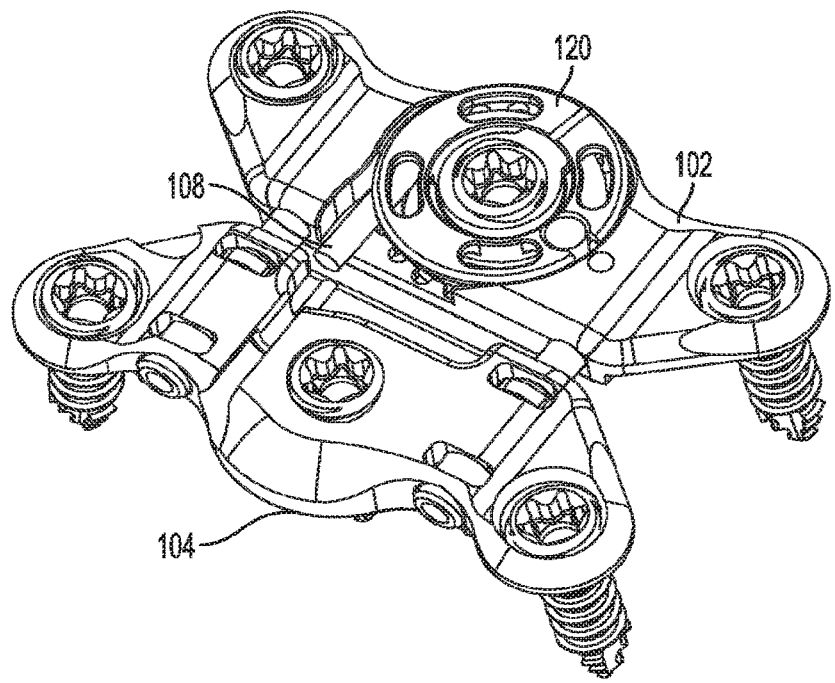
FIGS. 17 through 20 illustrate a locking element being cut and removed according to the disclosure.
Figure 18:
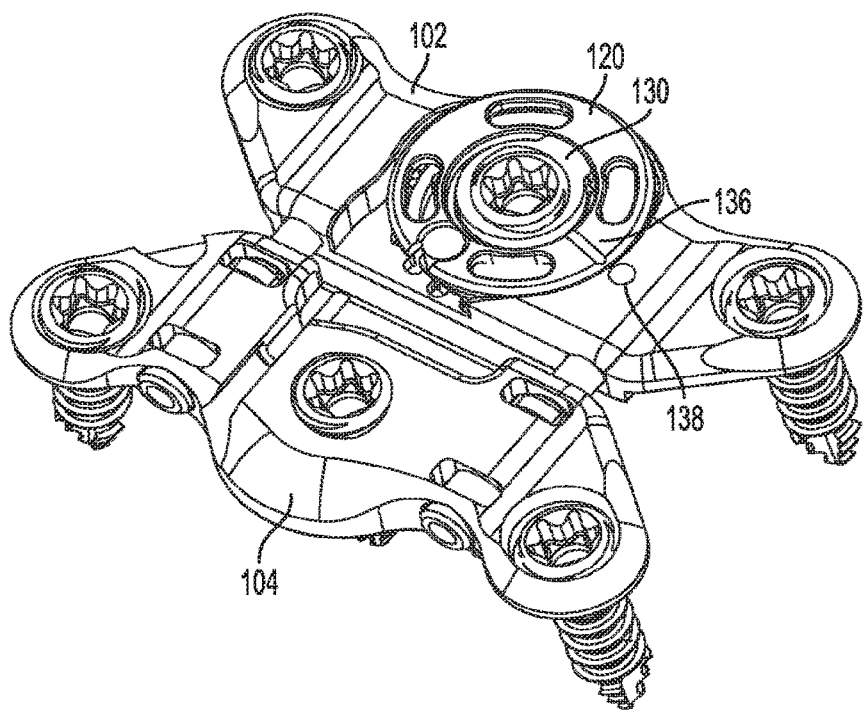
Figure 19:
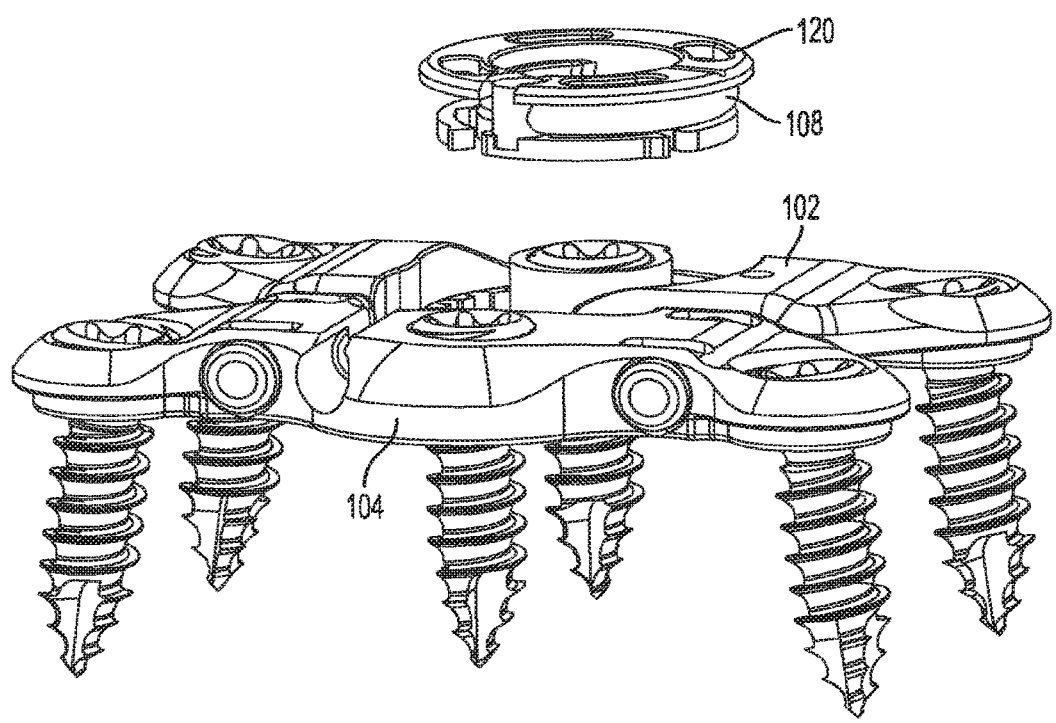

The steps described herein may be repeated for each implantable fixation device 100 that is used. When using multiple implantable fixation devices 100, the procedure may be repeated by alternating reduction incrementally from implantable fixation device 100 to implantable fixation device 100 until complete closure is achieved. For example, referring to FIG. 15, a middle implantable fixation device 100 may be incrementally tightened, a top implantable fixation device 100 may then be incrementally tightened, and then a bottom implantable fixation device 100 may be incrementally tightened. This may be repeated until the sternum is completely closed and the implantable fixation devices 100 are tightened together.

Once the implantable fixation device(s) 100 are tightened, the soft tissue may be closed in a normal fashion. It should be appreciated that sternal/cerclage wires may also be used in conjunction with the implantable fixation device(s) 100 if desired.

If emergency reentry is necessary, the fixation device(s) 100 allow for rapid access to the chest cavity. One option is to cut the locking element 108. Referring to FIGS. 16-22, the locking element 108 may be cut, for example using surgical scissors or other tool, illustrated as block 1602 and in FIG. 17. The ratchet wheel 120 may then be rotated to align the indicator 136 on the ratchet wheel 120 and the indicator 138 on the first plate 102, illustrated as block 1604 and in FIG. 18. As described above, when the indicators 136 and 138 are aligned, the cut-out 130 is aligned with the protrusion 132 (illustrated in FIG. 2). The ratchet wheel 120 may then be removed from the first plate 102, along with the cut portion of the locking element 108 engaged with the ratchet wheel 102, illustrated as block 1606 and in FIG. 19.

Figure 20:
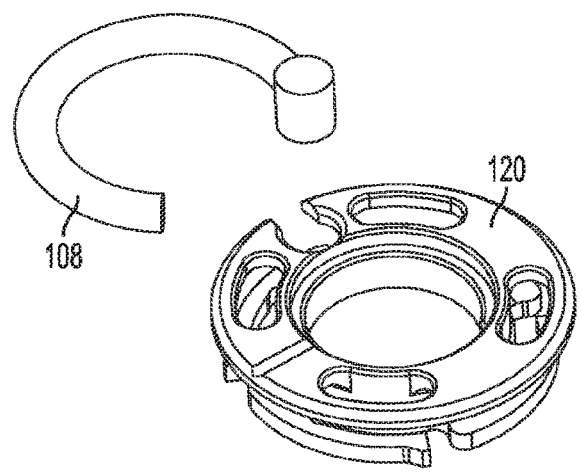
Figure 21:
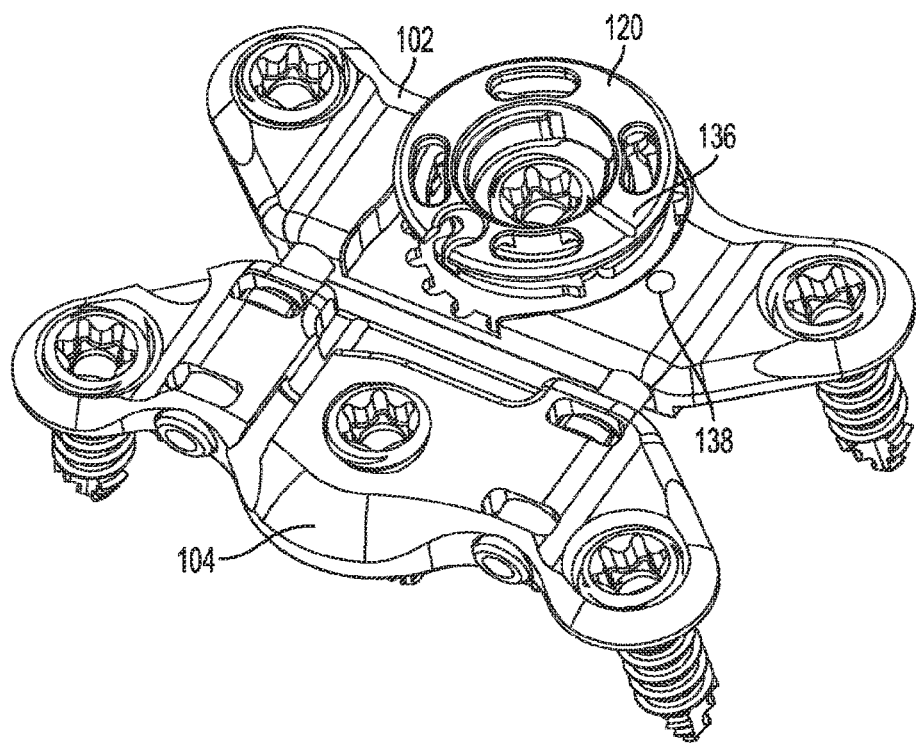
FIGS. 21 and 22 illustrate the ratchet wheel being reinstalled after removal of the locking element.
Figure 22:
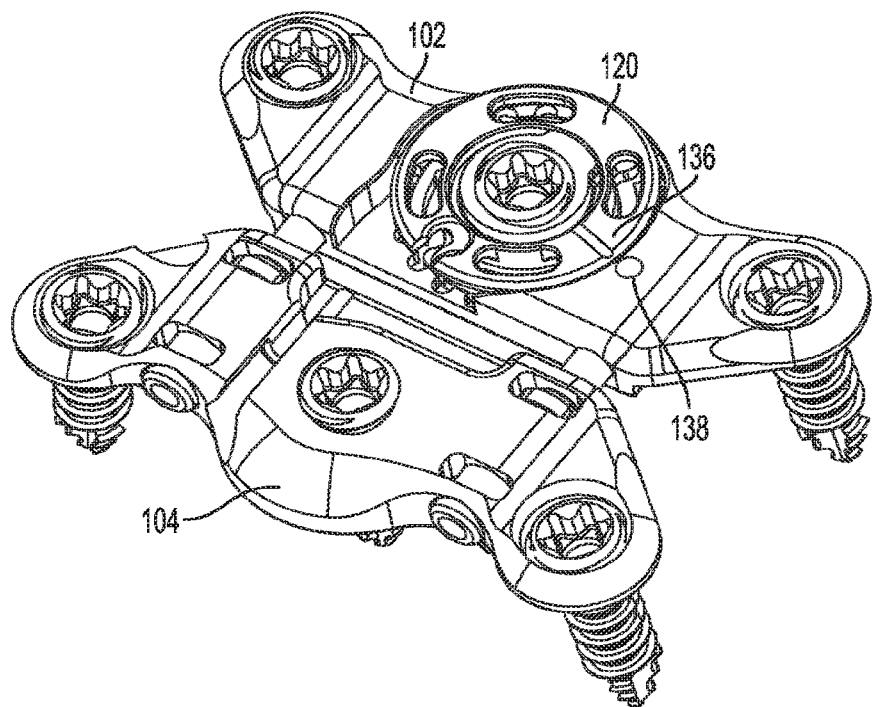

The coiled portion of the cut locking element 108 may then be removed from the ratchet wheel 120 and discarded, along with the corresponding portion of the cut locking element 108 from the second plate 104, illustrated as block 1608 and in FIG. 20. The ratchet wheel 120 may then be reinstalled in the first plate 102 by aligning the indicators 136 and 138, illustrated as block 1610 and in FIGS. 21 and 22. The ratchet wheel 120 may then be rotated to allow a new locking element 108 to be installed, illustrated as block 1612. The new locking element 108 may then be installed and the first and second plates 102 and 104 may be tightened to close the sternum as described above.

Another option is to remove the fasteners 150 and remove first and/or second plates 102 and 104 completely. If this option is used, the medial edges of the sternum may be brought into complete approximation using normal methods, including reduction instruments and or stainless steel wires. The first and second plates 102 and 104 may then be reinstalled with a new locking element 108 in accordance with the steps described above and illustrated in FIG. 9.

Although the devices, systems, and methods have been described and illustrated in connection with certain embodiments, many variations and modifications should be evident to those skilled in the art and may be made without departing from the spirit and scope of the disclosure. For example, the components described herein may be made of titanium or other material suitable for surgical procedures. Other materials may also be used depending on the application of use. Similarly, the shapes, sizes, and dimensions of the components may be scaled up or down or altered to suit a particular application. The discourse is thus not to be limited to the precise details of methodology or construction set forth above as such variations and modification are intended to be included within the scope of the disclosure.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for joining opposed parts of a bone or other body portion, comprising:
providing a first joinder member and a second joinder member;
attaching said first and second joinder members to a bone or other body portion along a divide which said joinder members are intended to reduce or close, with a space separating said joinder members, said space adapted to permit a surgical cutting tool to pass through said space and cut the underlying bone or body portion to create said divide;
providing a mechanism which engages said joinder members across said divide to reduce or close said divide;
creating said divide using a surgical cutting tool; and
reducing or closing said divide using said mechanism contemporaneously with said joinder members.

2. The method of claim 1, wherein openings are defined in each of said joinder members extending through a top and bottom sides of each said joinder member for receiving fixation elements for anchoring each said joinder member to an underlying bone or body portion, and further including a step of fixing said joinder members in place by anchoring said fixation elements to the underlying bone or body portion.

3. The method of claim 1, wherein said mechanism is a winding mechanism on said first joinder member having a rotary piece and an anchor point being formed on said rotary piece.

4. The method of claim 3, further including a step of providing a bendable elongated locking element having one end received by said anchor point, and another end attached to said second joinder member, said locking element spanning said divide, and said winding mechanism with said locking element received by said anchor point causing said locking element to wrap about said rotary piece as said rotary piece is rotated, and thereby drawing said joinder members into relative engagement as said winding mechanism is advanced.

5. The method of claim 4, wherein said winding mechanism is a ratchet mechanism comprising a wheel rotating on an axis with a pawl formed on said wheel that interacts with a ratchet element, and a latch being formed on said wheel as said anchor point.

6. The method of claim 1, further including a step of providing at least one stabilizing element, and the at least one stabilizing element having a part on one joinder member which inter-fits with another part on the other joinder member, the at least one stabilizing element spanning said divide.

7. The method of claim 6, wherein the at least one stabilizing element includes at least two stabilizing elements, said stabilizing elements comprising joinder bars mounted for movement on one of said joinder members and receiving receptacles for receiving a portion of each said joinder bar on the other of said joinder members, said joinder bars being spaced apart along said divide.

8. The method of claim 1, wherein said joinder members are each in the form of plates having generally planar tops and bottoms.

9. The method of claim 1, wherein the mechanism is a wheel.

\* \* \* \* \*